United States Patent [19]
Chan

[11] Patent Number: 5,360,396
[45] Date of Patent: Nov. 1, 1994

[54] APPARATUS AND METHOD FOR IMPROVED INSUFFLATION

[75] Inventor: Michael Chan, British Columbia, Canada

[73] Assignee: Andronic Devices Ltd., Richmond, Canada

[21] Appl. No.: 93,455

[22] Filed: Jul. 19, 1993

Related U.S. Application Data

[63] Continuation of Ser. No. 909,625, Jul. 7, 1992, abandoned.

[51] Int. Cl.$^5$ .......................................... A61M 37/00
[52] U.S. Cl. ........................................ 604/26; 604/23; 128/747
[58] Field of Search ................................ 604/23-26; 128/747

[56] References Cited

U.S. PATENT DOCUMENTS

| | | |
|---|---|---|
| 2,544,931 | 3/1951 | Marco . |
| 3,674,010 | 7/1972 | Falenks . |
| 3,771,552 | 11/1973 | Watanabe . |
| 3,858,572 | 1/1975 | Binard et al. . |
| 3,870,072 | 3/1975 | Lindemann . |
| 3,982,533 | 9/1976 | Wiest . |
| 4,048,992 | 9/1977 | Lindemann et al. . |
| 4,207,877 | 6/1980 | Marquardt . |
| 4,207,887 | 6/1980 | Hiltebrandt et al. ............ 604/26 |
| 4,464,165 | 8/1984 | Semm . |
| 4,464,169 | 8/1984 | Semm . |
| 4,676,774 | 6/1987 | Semm et al. ..................... 604/26 |
| 4,715,372 | 12/1987 | Philippbar et al. . |
| 4,735,603 | 4/1988 | Goodson et al. . |
| 4,966,578 | 10/1990 | Baier et al. ...................... 604/26 |
| 5,013,294 | 5/1991 | Baier ............................... 604/26 |
| 5,098,375 | 3/1992 | Baier ............................... 604/26 |
| 5,152,745 | 10/1992 | Steiner et al. ................... 604/26 |

FOREIGN PATENT DOCUMENTS

| | | |
|---|---|---|
| 2326734 | 6/1977 | France . |
| 2408912 | 9/1975 | Germany . |
| 2733650 | 2/1979 | Germany . |
| 2803646 | 8/1979 | Germany . |
| DE-A-3413631 | 10/1985 | Germany . |
| 729352 | 5/1955 | United Kingdom . |

OTHER PUBLICATIONS

*Evaluation, Laparoscopic Insufflators*, E.C.R.I. Health Devices, May 1992, vol. 21, No. 5, 143–179.

Primary Examiner—Ralph A. Lewis
Attorney, Agent, or Firm—Klarquist Sparkman Campbell Leigh & Whinston

[57] ABSTRACT

The flow of insufflating gas is adjustable and regulated to prevent excessive pressure in the body cavity. A filter removes particulate matter from the gas entering the body and removes bacterial and viral matter from the gas leaving the body cavity.

7 Claims, 2 Drawing Sheets

APPARATUS AND METHOD FOR IMPROVED INSUFFLATION

This application is continuation of application Ser. No. 07/909,625, filed on Jul. 7, 1992, now abandoned.

FIELD OF THE INVENTION

The present invention relates to an apparatus and method for improving the speed, safety and accuracy of insufflation of gas into a patient's body to facilitate endoscopic surgery without risking injury to patients due to over pressurization or infection from cross-contamination.

BACKGROUND OF THE INVENTION

Many devices are known in the art which provide means for supplying a pressurized gas, usually carbon dioxide, in a controlled manner for insufflating a patient during a surgical procedure. It is necessary to control both the flow rate and pressure of the insufflation gas during this process, in order to eliminate possible complications resulting from over pressurization of the patient's body cavity. Various methods for accurately determining the pressure within the patient's body cavity have been developed, some of which are described in the following U.S. Pat. Nos.:

- 5,013,294 (Bauer)
- 5,006,109 (Douglas et al)
- 4,874,362 (Wiest et al)
- 4,676,774 (Semm et al)
- 4,966,578 (Baler et al)
- 4,464,169 (Semm),
- 4,207,887 (Hiltebrandt)

All of the devices and methods known in the art are intended to provide a reasonably accurate indication of the actual pressure of the insufflation gas inside the patient's abdomen or other body cavity, and to cause additional insufflation gas to enter the patient's body if the actual pressure is less than the desired pressure.

During endoscopic surgery there are a number of external forces which may affect the pressure of the insufflation gas inside the body cavity including respiration by or mechanical ventilation of the patient, insertion and removal of tools and instruments from the body cavity and external forces applied to the patient's abdomen by the surgeon during the course of surgery. These external influences greatly affect the actual pressure in the body cavity.

It is desirable that an insufflation device be able to provide insufflation gas at a high flow rate, in order to quickly re-establish the correct pressure in the body cavity after insufflation gas is lost due to removal or insertion of a surgical instrument. Furthermore, it is recognized that an ideal insufflation device should be able to rapidly remove excess gas from the body cavity in the event that the pressure of the insufflating gas exceeds the desired level.

Insufflation devices known in the art will compensate for any decrease in the actual pressure in the body cavity by allowing additional gas to flow into the body cavity, but provide no means for allowing insufflation gas to be removed from the body cavity unless the actual pressure in the body cavity is much greater than the desired pressure. For example, although the insufflation pressure used for abdominal insufflation is typically 12 to 15 mmHg, the relief valve which is provided in most insufflating devices operates at 50 to 60 mmHg. In these devices, this relief valve is the only means provided by which the insufflating device can act to reduce the pressure of the insufflating gas in the patient's body cavity. Over pressurization is avoided by limiting the rate at which gas can flow from the insufflator into the body cavity, and by assuming that there will be gas leakage and absorption of gas within the body, both of which will tend to reduce the gas pressure. As these processes may remove gas at a lower rate than the insufflating device can supply replacement gas, there is a possibility that the actual pressure in the body cavity will exceed the desired pressure for extended periods of time.

Insufflating devices known in the art can not act to reduce the pressure in the body cavity due to the risk of cross contamination. If flow of gas out of the patient's body and into the insufflating device were permitted, bacterial and viral matter which may be present in the patient's body could be moved by the insufflation gas into the insufflating device, from where it can act as a source of infection to any patient with whom the insufflating device is subsequently used.

Contamination of the patient's body cavity can occur even if flow of gas back into the insufflating device is prevented. Recent studies (Douglas E. Ott, M.D., Georgia Biomedical Research Group, Macon, Ga.) have shown that insufflating gas provided by standard gas cylinders may be contaminated with both inorganic materials such as rust, copper, molybdenum and chromium, and with numerous organic contaminants, all of which could be introduced into the patient's body cavity during insufflation.

In summary, insufflation devices known in the art are not able to provide the high flow of insufflating gas which is desired by the endoscopic surgeon in part due to the lack of a means to relieve any over pressurization which may occur. Furthermore, any over pressurization which may occur as a result of patient respiration, external forces applied to the patient's body, manipulation of surgical instruments, or the operation of the insufflating device, may exist for long periods of time until leaks or absorption decrease the pressure of the insufflating gas in the body cavity. Pressure relieving means in existing insufflation devices are purposely set at a very high pressure in order to prevent flow of gas back into the insufflating device, which would cause cross-contamination and endanger patients. Existing insufflation devices also permit contaminants from the insufflation gas supply to enter the patient's body.

Summary of the Invention

The present invention provides an apparatus and teaches a method for providing insufflation gas to a body cavity at a high flow rate, while providing a means to relieve over pressurization without danger of cross contamination or introduction of contaminants into the patient's body.

The present invention provides apparatus for safe insufflation of a body cavity comprising: a means for reducing the pressure of an insufflating gas, typically carbon dioxide drawn from a high pressure reservoir, to a desired pressure; a pressure relieving device connected to the outlet of the pressure reducing means, which may be adjusted to release insufflating gas when the pressure of the gas exceeds the desired pressure; and a filter which will remove particulate matter which may exist in the gas coming from the high pressure reservoir and will remove particulate matter including bacterial and viral matter from gas leaving the patient's body and exiting the pressure relieving device.

Advantageously, the filter used in the present invention may be constructed of an inexpensive material so that it may be disposed of and replaced between surgical cases, so that cross-contamination is eliminated. Alternatively, the filter may be constructed of a material which can be easily cleaned or sterilized between uses.

Another advantage of the present invention is that the pressure relieving means and filter allow rapid removal of insufflating gas in the event that the body cavity is over pressurized, permitting insufflating gas to be introduced at high flow rates without danger of extended over pressurization occurring.

In addition, the present invention provides a method for safe insufflation of a body cavity, comprising the steps of: directing pressurized gas from a reservoir through an adjustable pressure reducer; directing the pressurized gas from the pressure reducer through an adjustable pressure reliever; adjusting the pressure reliever to allow the insufflating gas to escape if the pressure at the exit of the pressure reducer exceeds the pressure set by the pressure reducer; directing the insufflating gas into the patient's body cavity through a filter which removes particulate matter from gas entering the body cavity, and removes particulate, bacterial and viral matter from insufflating gas leaving the body cavity; and disposing of, or cleaning, the contaminated filter element before using the insufflating device with a new patient.

DESCRIPTION OF THE PREFERRED EMBODIMENT

Figure 1:
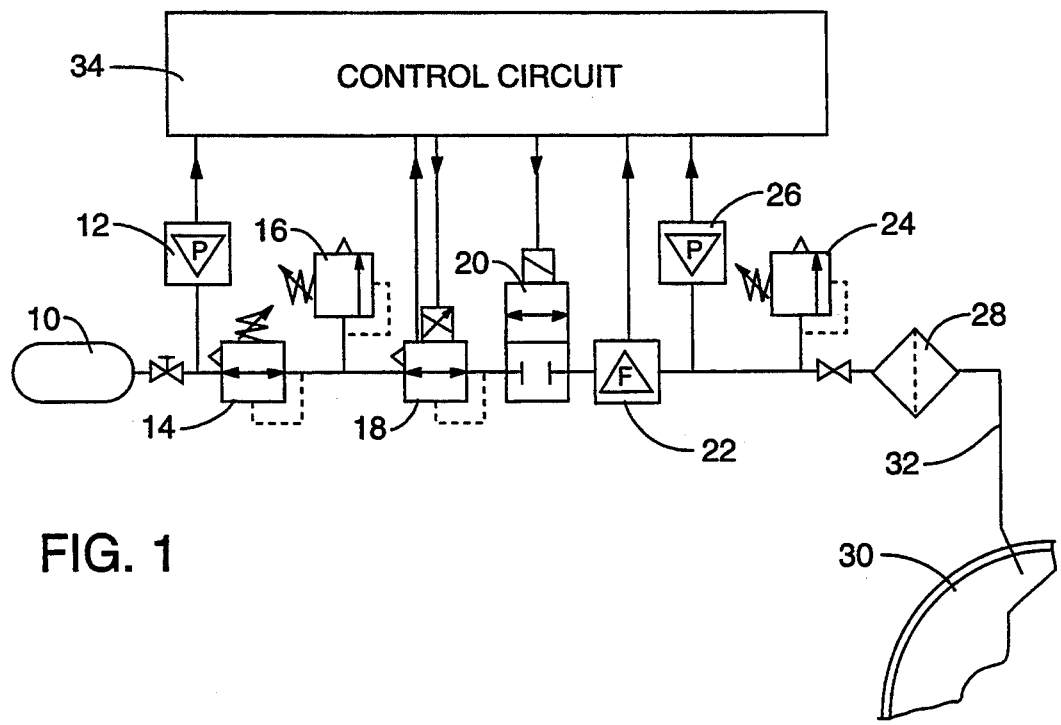
FIG. 1 is a schematic diagram of the pneumatic components of an insufflating device in accordance with the invention.

Referring to FIG. 1, carbon dioxide gas is supplied at a high pressure to the insufflator from $CO_2$ reservoir 10. This reservoir may be any size of high pressure gas cylinder intended for use with carbon dioxide. $CO_2$ reservoir 10 is connected to electronic high pressure sensor 12, which in the preferred embodiment is a Microgage model P149, capable of sensing pressures up to 2000 PSI. Also connected to $CO_2$ reservoir 10 is high pressure regulator 14, which in the preferred embodiment is a Norgren model R83200RNEA, which reduces the pressure of the $CO_2$ gas from $CO_2$ reservoir 10 to a pressure of 25 PSI. Connected to the output of high pressure regulator 14 is high pressure relief valve 16, which opens and exhausts $CO_2$ gas if the pressure exceeds 30 PSI. In the preferred embodiment, high pressure relief valve 16 is Circle Seal D533B-2M-F,30.

Also connected to output of high pressure regulator 14 is electronic pressure regulator 18, which in the preferred embodiment is a Bellofram 241-962 -095-000. This regulator incorporates an adjustable responds to an electronic control signal to supply an output pressure ranging from 0 to 55 mmHg, and a pressure reliever which opens to bleed off gas if the outlet pressure exceeds the pressure set by the pressure reducer component. The operation of electronic pressure regulator 18 is internally controlled by an electronic pressure sensor and a control circuit.

Connected to the outlet of electronic pressure regulator 18 is valve 20, which in the preferred embodiment is a normally closed valve, model 211-A-1/4 -F-BR-1/4, manufactured by Burkert. Valve 20 is connected in turn to flow transducer 22, (Honeywell, AWM5104VC), which provides an electronic signal proportional to flows of $CO_2$ ranging from 0 to 20 Standard Liters Per Minute (SLPM).

The outlet of flow transducer 22 is connected to relief valve 24, pressure transducer 26 and filter 28. In the preferred embodiment, relief valve 24 is a Circle Seal model 533B-2M-B relief valve which relieves pressures above 60 mmHg. Pressure transducer 26 is a Sensym SCX01 DN pressure sensor rated at 0 to 1 PSI.

Filter 28 is a 0.3 micron electret filter element made by 3M, enclosed in a housing which is connected to the outlet of flow transducer 22 such that all gas flowing out of flow transducer 22 in normal operation must pass through filter 28. The outlet of filter 28 is connected to the patient's body cavity 30 by means of hose 32. In the preferred embodiment, filter 28 is a custom filter element manufactured by Cybermedic of Denver Colo., although many other kinds of filter suitable for this application are available (Pall, Gelman Scientific, Marquest, Arbor Technologies, Fibretek and others).

Electronic sensor signals from high pressure sensor 12, flow transducer 22, pressure transducer 26 and electronic regulator 18 are all connected to control circuit 34. Electronic control signals from control circuit 34 are connected to electronic regulator 18 and valve 20.

Figure 2:
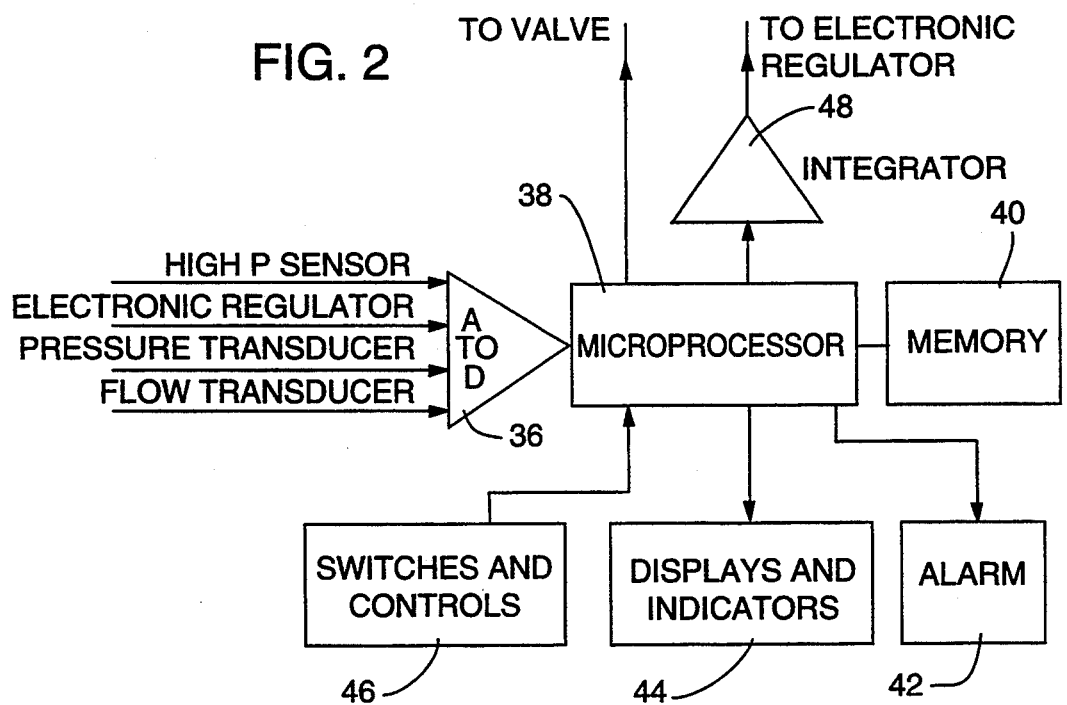
FIG. 2 is a block diagram of the electronic control system for the insufflator of FIG. 1.

Referring to FIG. 2, control circuit 34 consists of a microprocessor circuit, many examples of which are known in the art. Control circuit 34 includes analog to digital converter 36, which converts analog voltage signals from high pressure sensor 12, flow transducer 22, pressure transducer 26 and electronic regulator 18, into digital form for use by microprocessor 38. Microprocessor 38 also receives control information from switches and controls 46, and controls the operation of valve 20, integrator 48, displays and indicators 44 and alarm 42. Memory 40 provides program steps and calibration settings for microprocessor 38. Integrator 48 converts the variable pulse width signal from microprocessor 38 into a variable DC voltage to control electronic regulator 18.

Operation of Preferred Embodiment

In operation, the connection of gas supply 10 to the insufflation device causes high pressure sensor 12 to send a signal to analog to digital converter 36 indicating the amount of $CO_2$ pressure available in gas supply 10. Microprocessor 38 causes displays and indicators 44 to indicate the amount of gas remaining. High pressure regulator 14 reduces the pressure of the $CO_2$ gas to 25 PSI, which is directed to the input of electronic regulator 18. In the event that high pressure regulator 14 fails to regulate the $CO_2$ pressure below 30 PSI, relief valve 16 opens to allow the $CO_2$ gas to escape.

Microprocessor 38 reads switches and controls 46 to determine the desired insufflation pressure set by the user. This information, along with pressure and flow values detected by flow transducer 22 and pressure transducer 26, is used by microprocessor 38 to establish a desired control signal value for electronic regulator 18. Microprocessor 38 does this by sending a rapidly repeating pulse to integrator 48, the pulse width of which is calculated to cause integrator 48 to generate the desired control signal value for electronic regulator 18. This technique, widely known in the art as Pulse Width Modulation (PWM) permits microprocessor 38 to synthesize a continuous analog voltage from a digital (two state) output signal.

The software program stored in memory 40 controls the operation of microprocessor 38. The program algorithm used to determine the desired control signal value for electronic regulator 18 is a proportional integral derivative (PID) function which responds to the pressure values detected with pressure transducer 26. The output of the PID algorithm is further modified in response to the signal from flow transducer 22. If the flow rate measured by flow transducer 22 exceeds the maximum flow rate set by the user, microprocessor 38 decreases the output of electronic pressure regulator 18 to reduce the flow to acceptable levels.

The software program in memory 40 also causes microprocessor 38 to detect various abnormal conditions. One such condition is a leakage of gas from the patient's body cavity at a rate too high to be replenished by the insufflator This condition is considered to exist if microprocessor 38 fails to detect any increase in pressure sensed by pressure transducer 26 while the flow sensed by flow transducer 22 is at or near the maximum flow rate set by the user. If this condition continues for a set period of time, microprocessor 38 turns on one of displays and indicators 44 and alarm 42 to indicate a leak.

Microprocessor 38 also detects and warns of kinks in the hosing between the insufflator and the body cavity. To determine the existence of this condition, the output of electronic regulator 18 is increased for a short period of time. If pressure transducer 26 detects a very rapid increase in pressure, indicative of a very small volume connected to the outlet of electronic pressure regulator 18, a kink condition is deemed to exist. This condition is indicated on displays and indicators 44 and with alarm 42.

Excessive pressure in the patient's body cavity for any reason is immediately sensed by pressure transducer 26. If this pressure exceeds 30 mmHg at any time, microprocessor 38 immediately indicates this condition with displays and indicators 44 and alarm 42. In addition, microprocessor 38 will indicate an over pressure alarm if the PID control function is unable to cause the pressure sensed by pressure transducer 26 to return to within 3 mmHg of the pressure selected by the user within a fixed time period.

As an additional check on the function of electronic regulator 18, a signal from electronic regulator 18, representative of the pressure detected by its internal pressure sensor, is directed through analog to digital converter 36, to microprocessor 38. This signal is also used by microprocessor 38 to check the function of pressure transducer 26.

The gas output of electronic regulator 18 is directed into normally closed valve 20. This valve is selected to close off the supply of gas to the patient's body in the event of a power failure or other failure of the insufflator. Valve 20 can also be closed by microprocessor 38 so that the actual pressure in the patient's body cavity can be checked with pressure transducer 26 at any time.

Also connected to analog to digital converter 36 are signals from flow transducer 22 and pressure transducer 26. These signals are converted to digital form and directed to microprocessor 38, so that microprocessor 38 can monitor the flow rate of gas to the patient and measure the insufflation pressure being used at any time.

Connected to the outlet of flow transducer 22 is relief valve 24, which will open and exhaust gas if the pressure exceeds 60 mmHg. This valve is intended to act as a safety relief in the event that pressure in the patient's body cavity exceeds this pressure for any reason.

Displays and indicators 44 are controlled by microprocessor 38 to display information which may be useful to the surgeon, including the insufflation pressure, the actual abdominal pressure, the flow rate of gas into the patient, the total volume of gas insufflated, and the total insufflation time.

Alarm 42 may be turned on by microprocessor 38 in the event that the insufflation pressure exceeds a set value, if leaks or occlusions in insufflation hose 32 occur, or if the supply of gas in CO2 reservoir 10 falls below a minimum acceptable level.

Figure 3:
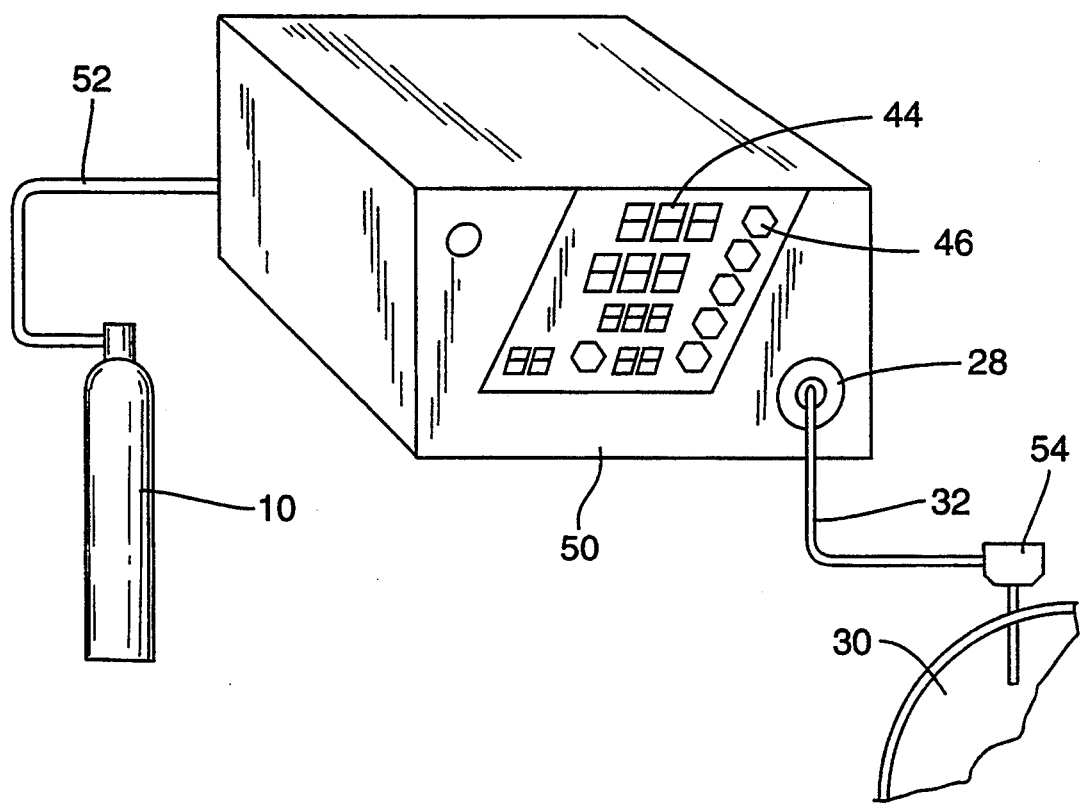
FIG. 3 is a pictorial drawing of the insufflator of FIG. 1 in use.

Referring to FIG. 3, insufflator 50 is typically connected to gas supply 10 with high pressure hose 52. Filter 28 is connected to insufflator 50 and to insufflation hose 32, which is connected in turn to patient's body cavity 30 through trocar 54. Typically, filter 28 and insufflation hose 32 are constructed of inexpensive, stedle material which may be disposed of after each surgical procedure.

In use, the surgeon uses switches and controls 46 to set the desired pressure in the patient's body cavity and the maximum allowable gas flow rate, and then begin the insufflation. Displays and indicators 44 continuously display the pressure in the body cavity, the flow rate, time and other information useful to the surgeon.

Many adaptations and variations to the present invention are possible, Accordingly, the invention is to be limited only by reference to the appended claims. For example, although the preferred embodiment described is intended for use with carbon dioxide gas, other gasses such as helium or nitrous oxide may be used. Various means for controlling the flow of gas so as to allow relief of pressure above the desired pressure can be contrived. Although the filter used in the preferred embodiment is a 0.3 micron electret type, filter means of various pore sizes and types could be used to remove particles of various sizes.

We claim:

1. An insufflating apparatus comprising:
   a source of pressurized gas;
   an elongated conduit connected to the source for conducting the gas from the source, the conduit having a distal end adaptable for directing the gas into and out of a body cavity;
   a regulator connected to the conduit so that the gas from the source flows through the regulator to the distal end, the regulator being responsive to an electronic signal for increasing and decreasing the gas pressure in the conduit for maintaining the gas pressure in the conduit within a pressure range defined by a minimum pressure level and a maximum pressure level, the regulator decreasing the pressure by bleeding gas from the conduit; and
   a safety relief valve connected to the conduit between the source and the distal end for relieving gas pressure within the conduit whenever the pressure within the conduit exceeds a second pressure level that is substantially higher than the maximum pressure level of the pressure range.

2. The apparatus of claim 1 further comprising a filter replaceably connected to the conduit between the regulator and the distal end, the conduit defining the only path for gas flow between the filter and the distal end, and the filter being constructed for filtering the gas irrespective of the direction the gas travels within the conduit.

3. The apparatus of claim 2, including a shutoff valve connected to the conduit near the distal end and wherein the filter is connected between the shutoff valve and the distal end, the shutoff valve being operable to stop gas flow through the conduit, thereby facilitating the replacement of the filter.

4. The apparatus of claim 1, wherein the pressure range is about 6 mmHg.

5. The apparatus of claim 1, including a second safety relief valve connected to the conduit between the distal end and the regulator for relieving gas pressure within the conduit whenever the pressure within the conduit exceeds a second pressure level that is substantially higher than the maximum pressure level of the pressure range.

6. A method of safely insufflating a gas into and out of a body cavity, comprising the steps of:

providing a source of pressurized gas;

conducting gas from the source through a conduit and into a body cavity;

connecting a safety relief valve to the conduit between the source and the body cavity to relieve gas pressure in the conduit in the event the gas pressure in the conduit exceeds a first pressure level;

regulating the pressure in the conduit by maintaining the gas pressure in the conduit within a pressure range defined by a minimum pressure level and a maximum pressure level, the maximum pressure level being substantially lower than the first pressure level, and by bleeding gas from the conduit in response to the gas pressure in the conduit exceeding the maximum pressure level; and filtering the gas in the conduit with a filter that filters the gas irrespective of the direction the gas flows in the conduit.

7. The method of claim 6 further comprising the step of replaceably connecting the filter to the conduit for facilitating replacement of the filter after each insufflating procedure.

* * * * *